United States Patent [19]

Stapp

[11] 4,159,967

[45] Jul. 3, 1979

[54] CATALYST FOR THE OXIDATION OF A CONJUGATED DIOLEFIN

[75] Inventor: Paul R. Stapp, Bartlesville, Okla.

[73] Assignee: Phillips Petroleum Company, Bartlesville, Okla.

[21] Appl. No.: 883,014

[22] Filed: Mar. 3, 1978

Related U.S. Application Data

[62] Division of Ser. No. 721,645, Sep. 8, 1976, Pat. No. 4,095,037.

[51] Int. Cl.$^2$ .................. B01J 23/04; B01J 27/08; B01J 27/24; B01J 31/12
[52] U.S. Cl. .......................... 252/438; 252/431 C; 252/441; 252/476
[58] Field of Search ............... 252/431 C, 438, 476, 252/441

[56] References Cited

U.S. PATENT DOCUMENTS

| | | | |
|---|---|---|---|
| 3,238,225 | 3/1966 | Brill et al. | 252/464 X |
| 3,432,558 | 3/1969 | Ryland | 260/604 R |
| 3,670,014 | 6/1972 | Fernholz et al. | 560/245 |
| 3,755,423 | 8/1973 | Onoda et al. | 560/1 |

Primary Examiner—W. J. Shine

[57] ABSTRACT

A conjugated diolefin is reacted with a carboxylic acid, a carboxylic acid anhydride, or a mixture thereof, in the presence of oxygen and a catalyst comprising a compound of bismuth, an alkali metal compound and a source of nitrate ion.

6 Claims, No Drawings

CATALYST FOR THE OXIDATION OF A CONJUGATED DIOLEFIN

This application is a division of my copending application Ser. No. 721,645, filed Sept. 8, 1976, now U.S. Pat. No. 4,095,037.

BACKGROUND OF THE INVENTION

The invention relates to a method suitable for the oxidation of a conjugated diolefin. In another aspect, the invention relates to a composition useful as a catalyst.

It is desirable to oxidize conjugated diolefins, such as 1,3-butadiene and/or 2-methyl-1,3-butadiene to produce various compounds such as the ethylenically unsaturated esters. An example is the oxidation of 1,3-butadiene to produce 1,4-diacetoxy-2-butene. The diacetoxybutene is then easily converted, by processes well known in the art, to other compounds such as tetrahydrofuran or 1,4-butanediol. Although there are various processes and catalysts known which are useful for the oxidation of a conjugated diolefin, most of these processes are relatively expensive to carry out and frequently corrosion of process equipment is a problem. Therefore, new processes and catalysts are desirable in an effort to more fully develop the art and improve the overall process.

An object of the present invention is to oxidize a conjugated diolefin.

Another object of the invention is to oxidize a conjugated diolefin more economically than can be done presently.

Another object of the invention is to oxidize a conjugated diolefin with minimum corrosion of process equipment.

Another object of the invention is to provide a catalyst useful for the oxidation of conjugated diolefins.

Other objects, advantages and aspects of the present invention will be apparent to those skilled in the art after studying the specification and appended claims.

SUMMARY OF THE INVENTION

In accordance with the invention, a conjugated diolefin is reacted with a carboxylic acid, a carboxylic acid anhydride, or a mixture thereof, in the presence of oxygen and a catalyst comprising a compound of bismuth, an alkali metal compound, and a source of nitrate ion. In order to simplify the purification and separation steps, it is preferred to use both a carboxylic acid and a carboxylic acid anhydride, which corresponds to the carboxylic acid.

Further in accordance with the invention, a composition comprises a compound of bismuth, an alkali metal compound, and a source of nitrate ion.

DETAILED DESCRIPTION OF THE INVENTION

The conjugated diolefins suitable for use in the process of the invention are selected from a wide range of compounds. Generally the conjugated diolefins employed in the process of the instant invention are those having from 4 to 16 carbon atoms per molecule. Suitable conjugated diolefins include acyclic, as well as cyclic compounds, and further include compounds which have substituents such as halogen, cyano, or carbalkoxy radical present in the molecule.

Some suitable acyclic conjugated diolefins are represented by the following general formula:

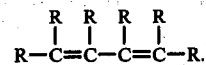

In said formula 1), R— is selected from the group consisting of H—, F—, CL—, Br—, I—,

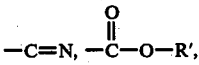

and the monovalent hydrocarbyl radicals of up to 12 carbon atoms such as alkyl, aryl, cycloalkyl and combinations such as alkaryl, aralkyl, cycloalkylaryl and the like. For the group

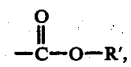

—R' is selected from the group consisting of —H, alkyl, and the aryl radicals of up to 10 carbon atoms. It is understood that the total number of carbon atoms in all substituents (R—) combined will not exceed 12.

Some suitable cyclic conjugated diolefins are represented by the following general formula:

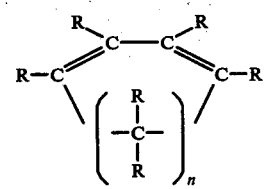

Said cyclic conjugated diolefins contain from 5 to 16 carbon atoms per molecule. In said formula 2), R— has the same meaning as the formula 1), and n is an integer having a value of from 1 to 12. It is further understood that the total number of carbon atoms in all substituents (R—) combined will not exceed 11.

Presently preferred conjugated diolefins are those containing only carbon and hydrogen because use of such materials produces products finding particular applicability today. For the same reason, the compounds especially preferred for use in the instant invention are 1,3-butadiene and 2-methyl-1,3-butadiene (isoprene) to produce the corresponding 1,4-diacetoxy derivatives. Examples of suitable conjugated diolefins include 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 1,3-cyclohexadiene, 1,3-cyclooctadiene, 1,3-cyclododecadiene, 2-cyano-1,3-butadiene, 2-carbethoxy-1,3-butadiene, cyclopentadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 2-cyclohexyl-1,3-butadiene, 2-methylene-3-butenoic acid and 2,4-pentadienenitrile.

Mixtures of conjugated olefins are also suitable; however, a mixture of products will result which may be difficult to separate into the individual component products.

The conjugated diolefin is reacted with at least one compound selected from the group consisting of a carboxylic acid and a carboxylic acid anhydride to produce the corresponding diacyloxyalkene. In most instances, it is preferred to use a carboxylic acid and the corresponding acid anhydride because the use of the corresponding acid anhydride, in addition to the carboxylic acid, serves to simplify the purification and separation steps by reducing the amount of by-products which contain free hydroxy groups. However, it is within the scope of the invention to use a carboxylic acid alone, a carboxylic acid anhydride alone, a carboxylic acid and a carboxylic acid anhydride of a different carboxylic acid or a carboxylic acid and the corresponding acid anhydride. If the reaction is carried out using a carboxylic acid and a carboxylic acid anhydride of a different carboxylic acid, a mixture of reaction products normally results.

The carboxylic acids and acid and acid anhydrides suitable for use in the invention are selected from a large variety of compounds. Generally, the acids and acid anhydrides include mono- and dicarboxylic acids and acid anhydrides having from about 2 to about 18 carbon atoms per molecule. Such compounds include both aromatic and aliphatic compounds. Furthermore, they can contain halogen or cyano groups or other substituents which are essentially inert to the oxidizing conditions employed for the process of this invention. It is preferred, of course, that the carboxylic acid employed be normally liquid or at least liquid under the conditions employed for the reaction for ease in handling.

Some suitable monocarboxylic acids for use in the instant invention are represented by the general formula:

$$R''\text{—CO}_2H \qquad (3)$$

wherein R" is selected from the group of radicals consisting of alkyl, aryl, cycloalkyl or combinations such as alkaryl, aralkyl, cycloalkylaryl and the like, or halogen-, cyano- or

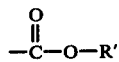

substituted derivatives thereof wherein up to 4 of said halogen, cyano or

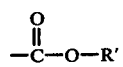

substituents can be present in said radical. Furthermore, said monocarboxylic acids contain from 2 to 18 carbon atoms per molecule. The group R'— has the same meaning as that given in the discussion of general formula (1) above.

Some suitable dicarboxylic acids for use in this invention are represented by the following general formula:

$$R'''\,(\text{CO}_2H)_2 \qquad (4)$$

wherein R''' is selected from the group consisting of a valence bond, the radicals alkylene, arylene, cycloalkylene or combinations such as alkarylene, aralkylene, cycloalkylarylene and the like or halogen-, cyano-, or

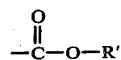

substituted derivatives thereof wherein up to 4 of said halogen, cyano or

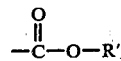

substituents can be present in said radical. The dicarboxylic acids also contain from 2 to 18 carbon atoms per molecule. The group R' has the same meaning as that given in the discussion of general formula (1) above.

Acetic acid and acetic anhydride are presently the preferred carboxylic acid and acid anhydride for use according to the process of this invention. Examples of other suitable carboxylic acids and acid anhydrides include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid and ethyl hydrogen-o-phthalate, and the respective acid anhydrides. Mixtures of carboxylic acids and acid anhydrides can be used; however, a mixture of reaction products normally results.

The oxidation catalyst employed in accordance with the invention comprises a compound of bismuth, a compound of an alkali metal and a source of nitrate ion. The bismuth compound can be in the form of nitrates, oxides, halides and mixtures thereof. Examples of suitable bismuth compounds include bismuth nitrate, bismuth oxychloride, bismuth oxyfluoride, bismuth oxynitrate, bismuth tribromide, bismuth trichloride, bismuth trifluoride, bismuth triiodide, and bismuth trioxide.

The second component of the catalyst system of this invention is a compound of an alkali metal such as a halide, carboxylate, oxide, nitrate, and mixtures thereof. Of the alkali metal compounds, which can be employed, the lithium compounds are especially preferred for use as the alkali metal component for the process of this invention because they generally have very high solubility in organic solvents as compared to other alkali metal compounds. Examples of suitable alkali metal compounds which can be employed include lithium chloride, lithium bromide, lithium iodide, lithium acetate, lithium benzoate, lithium oxide, lithium octadecanoate, lithium nitrate, sodium chloride, sodium bromide, sodium acetate, potassium chloride, sodium nitrate, potassium acetate, potassium benzoate, potassium nitrate, rubidium chloride, rubidium bromide, rubidium acetate, rubidium nitrate, cesium chloride, cesium acetate, cesium oxide, and cesium nitrate. Mixtures of the alkali metal compounds may also be employed.

The third component of the catalyst system of this invention is the nitrate ion. The nitrate ion requirement of the catalyst system of this invention can be furnished at least in part by a bismuth nitrate and/or an alkali metal nitrate or by the addition of another inorganic compound providing a source of nitrate ion, e.g., $HNO_3$. Furthermore, an inorganic compound of some other element can be added to furnish the source of nitrate ion. Such compounds which can be added include those in which the cationic portion of the compound is essentially inert to the oxidizing conditions employed in the process of this invention.

The gram equivalent ratio of nitrate ion to bismuth and also the gram equivalent ratio of alkali metal to bismuth for the instant invention can be selected over a wide range of ratios. Generally, the ratio of alkali metal to bismuth and nitrate ion to bismuth range from about 0.1/1 to about 25/1. Based upon the results of runs hereinafter described, good results can be obtained employing a ratio ranging from about 1/1 to about 10/1.

The concentration of catalyst employed for the oxidation reaction of this invention is expressed in terms of the mole percent bismuth compound based on the amount of conjugated diolefin employed. The catalyst is effective over a wide range of catalyst concentrations. The catalyst concentration generally ranges from about 0.1 to about 50 mole percent of bismuth compound based on the amount of conjugated diolefin charged. Also based upon the results of runs hereinafter described, good results can be obtained employing a catalyst concentration ranging from about 1 to about 15 mole percent of bismuth compound based on the amount of conjugated diolefin charged.

The reaction of the instant invention is an oxidation reaction and as such is carried out in the presence of free oxygen. The amount of oxygen present is not believed to be critical, although it is recognized that an undesirably slow reaction will result if the concentration of oxygen is very low. Essentially pure oxygen can be employed, as well as mixtures of oxygen with inert gases, or air can be employed as a source of free oxygen for the instant reaction. It is recognized that explosive conditions could be obtained if the amount of oxygen added to the reaction system were not under control. The reaction of this invention, as is true with many oxidation reactions, appears to be highly exothermic and this too dictates caution in adding oxygen to the system. Because of these considerations, it is desirable to add the oxygen incrementally or continuously during the reaction to avoid the explosive range of oxygen concentration and to allow better control of the temperature of the reaction. A reaction vessel with efficient mixing means is also desirable to avoid buildup of dangerous concentrations of free oxygen.

The temperature at which the reaction of this invention is carried out is selected over a relatively wide temperature range. Generally, a temperature range of from about 30° to about 200° C. is employed. In view of the temperature employed in the runs described herein, temperatures ranging from about 100° to about 150° C. can be used with good success.

Similarly, the oxygen pressure reaction at which the reaction is carried out can be selected over a relatively wide range. Generally, the oxygen pressure ranges from about 0.1 to about 1000 psig of oxygen above autogenous pressure of the reactants in the absence of oxygen at the temperature employed; however, the results of the runs made in accordance with the invention indicate that good results can be obtained employing a range from about 5 to about 200 psig of oxygen above autogenous pressure at the temperature employed.

The reaction time generally depends on the temperature, catalyst activity, the reactants, and the oxygen pressure employed. The reaction time is usually based on the desired conversion of the starting diolefin reactant. The reaction time does not appear to be a particularly signficant parameter of the reaction and in some cases a product can probably be produced at very low yields using a reaction time as short as a second; however, much longer reaction times are normally used ranging from about 1 to about 12 hours. The good results obtained in the runs described herein indicate that a reaction time ranging from about 3 to about 8 hours can be used.

As described above, the reaction of the instant invention is carried out in the presence of a carboxylic acid and/or acid anhydride which provides the acyl portion of the final product. In most instances, as previously described, it is desirable to employ as part of the reaction mixture the corresponding carboxylic anhydride (in addition to the carboxylic acid) as an optional but preferred component because the carboxylic acid anhydride serves to simplify the purification and separation steps by reducing the amount of by-products which contain free hydroxy groups. When both a carboxylic acid and the corresponding acid anhydride are used, it is desirable to use at least an amount of the acid anhydride equal to the amount of conjugated diolefin on a molar basis because for each mole of the diacyloxyalkene produced, one mole of water is also produced.

The process of the instant invention can be carried out in a batch or a continuous fashion.

Reaction mixtures obtained according to the process of this invention are generally vented to remove any unreacted oxygen and conjugated diolefin and then distilled to remove the carboxylic acid present. The product remaining is usually distilled to recover one or more fractions containing the diacyloxy olefins. The catalyst is usually recovered from the distillation residue and recycled to the reaction zone.

The isomeric materials which are recovered from the product mixture include in many instances an amount of 1,2-isomer which can be recycled to the reaction zone and thereby converted to the more desirable 1,4-diacyloxy olefin. Also any unreacted conjugated diolefin recovered from the reaction mixture can be recycled to the reaction zone.

The above-mentioned 1,4-diacyloxy olefins have utility as intermediates for the preparation of the corresponding saturated diols. For example, as previously noted, it is known to prepare tetrahydrofuran or 1,4-butanediol starting with 1,3-butadiene and proceeding through 1,4-diacyloxy butene.

EXAMPLE I

A run was carried out according to the process of this invention by charging a 250 ml Fisher-Porter aerosol compatibility bottle equipped with a magnetic stirrer with 4.6 grams (21.5 mmoles) of 1,4-dibromo-2-butene, 3.9 grams (50 mmoles) of lithium nitrate, 4.7 grams (10 mmoles) of bismuth trioxide, 50 ml of acetic acid and 25 ml of acetic anhydride and 10.5 grams (194 mmoles) of butadiene charged in the vapor phase. The reaction vessel was pressured to 30 psig with oxygen, placed in an oil bath and heated to 140° C. About 1 hour was required for the reaction vessel to reach 140° C. reaction temperature. Subsequently the reaction was carried out for 5.8 hours during which oxygen was added to the reactor intermittently by pressuring the reactor to 120 psig at about 20 minute intervals. At the end of the reaction period, the reactor was vented, and a black solid material filtered from the reaction mixture. The filtrate was distilled through an 18″ Vigreaux column to remove acetic acid. The distillation residue was mixed with water and ether, and the aqueous layer extracted several times with ether. The combined ether extracts were washed with water, a sodium carbonate solution, dried over magnesium sulfate, filtered, and the ether removed on a rotary evaporator. The residue remaining weighed 10.0 grams. This residue was analyzed by gas-liquid phase chromatography which indicated that there was obtained 3.14 grams (18.3 mmoles) of 1,2-diacetoxy-3-butene and 3.97 grams (23.1 mmoles) of 1,4-diacetoxy-2-butene for a combined yield of the diacetoxy butenes of 21% based on the butadiene charged. This result demonstrates the operability of the catalyst system of this invention for producing diacyloxy olefins from conjugated diolefin reactants.

EXAMPLE II

A control run was conducted employing the same apparatus as that utilized in Example I. In this run, the reactor was charged with 4.6 grams (21.5 mmoles) of 1,4-dibromo-2-butene, 6.5 grams (75 mmoles) of lithium bromide, 9.3 grams (20 mmoles) of bismuth trioxide, 25 ml of acetic anhydride, 50 ml of acetic acid, and 10.4 grams (193 mmoles) of butadiene charged in the vapor phase. The reactor was pressured to 30 psig with oxygen, placed in an oil bath and heated to 140° C. for 4 hours. During this reaction period, the reactor pressure showed essentially no decrease indicating that very little reaction had occurred. The reactor was therefore vented and the contents discarded without further analysis. This result demonstrates the poor reaction rate obtained in the absence of nitrate ion.

EXAMPLE III

Another control run was carried out, employing the same reaction vessel as that utilized in Examples I and II above. In this run, the reactor was charged with 3.9 grams (50 mmoles) of lithium nitrate, 50 ml of acetic acid, 25 ml of acetic anhydride, and 11.0 grams (204 mmoles) of butadiene charged from the vapor phase. The reactor was placed in an oil bath and pressured to 30 psig with oxygen, and heated to 140° C. for 3 hours. Oxygen was added to the reactor intermittently in the same manner as in Example I. At the end of the reaction period, the reactor was vented and the contents fractionally distilled through an 18" Vigreaux column, fraction 1 boiling at 46–51° C. at 55 mm Hg, weighed 88.4 grams while fraction 2 boiling at 74–78° C. at 6 mm Hg, weighed 2.1 grams and the distillation residue fraction 3 weighed 17.7 grams and was a thick black tar. Fractions 1 and 2 were analyzed by gas-liquid phase chromatography, which indicated that there was obtained 1.16 grams (6.7 mmoles) of 1,2-diacetoxy-3-butene and 0.43 grams (2.5 mmoles) of 1,4-diacetoxy-2-butene for a total yield of 9.2 mmoles of the diacetoxy butenes. This represents a yield of 4.5% based on the butadiene charged. This result shows that a much lower yield of diacetoxy butenes was obtained when the bismuth catalyst component is omitted from the reaction mixture.

EXAMPLE IV

Another control run was conducted employing the same reaction apparatus as that used in the previous examples. In this run, the reactor was charged with 4.6 grams (21.5 mmoles) of 1,4-dibromo-2-butene, 3.9 grams (50 mmoles) of lithium nitrate, 50 ml of acetic acid, 25 ml of acetic anhydride and 11.5 grams (213 mmoles) of butadiene charged in the vapor phase. The reaction vessel was placed in an oil bath, pressured to 30 psig with oxygen and heated as in the previous runs. When the temperature reached about 130° C. with a pressure of about 95 psig, a vigorous reaction suddenly ensued with the temperature rising rapidly to 149° C. and the pressure to 180 psig. Copious amounts of brown fumes (presumably $NO_2$) were also noted at this time. Because of the possible danger of explosion with the apparently uncontrolled reaction, the reactor was removed from the heating bath and the reaction discontinued. The reaction mixture was discarded. This result indicates that in the absence of the bismuth component and in the presence of the dibromo butene, the lithium nitrate in the presence of oxygen apparently undergoes an exothermic decomposition with the attendant possibilities of an explosion. This type of result is, of course, undesirable when it is desired to carry out an oxidation of conjugated diolefins in the presence of carboxylic acids to produce diacyloxy olefins.

What is claimed is:

1. A composition consisting essentially of a bismuth compound, an alkali metal compound and a source of nitrate ion wherein the bismuth compound is selected from the group consisting of oxides, nitrates, halides and mixtures thereof, the alkali metal compound is selected from the group consisting of halide, carboxylate, oxide, nitrate and mixtures thereof, and the source of nitrate ion is provided by an inorganic compound in which the cationic portion of the compound is essentially inert under oxidizing conditions when said cationic portion is other than bismuth or an alkali metal.

2. A composition according to claim 1 wherein the source of nitrate ion is furnished by either or both the bismuth compound and the alkali metal compound.

3. A composition according to claim 1 wherein the bismuth compound is selected from the group consisting of bismuth nitrate, bismuth oxychloride, bismuth oxyfluoride, bismuth oxynitrate, bismuth tribromide, bismuth trichloride, bismuth trifluoride, bismuth triiodide, bismuth trioxide; and the alkali metal compound is selected from the group consisting of lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, and mixtures thereof.

4. A composition according to claim 1 wherein the gram equivalent ratio of nitrate ion to bismuth and the gram equivalent ratio of alkali metal to bismuth is within a range of about 0.1:1 to about 25:1.

5. A composition according to claim 1 wherein the gram equivalent ratio of nitrate ion to bismuth and the gram equivalent ratio of alkali metal to bismuth is within a range of about 1:1 to about 10:1.

6. A composition according to claim 1 wherein the bismuth compound is bismuth trioxide and the alkali metal compound and the source of nitrate ion are lithium nitrate.

* * * * *